United States Patent [19]

Becker et al.

[11] Patent Number: 4,602,935
[45] Date of Patent: Jul. 29, 1986

[54] CYCLOHEXANE-1,3-DIONE DERIVATIVES AND THEIR USE FOR CONTROLLING UNDESIRABLE PLANT GROWTH

[75] Inventors: Rainer Becker, Bad Duerkheim; Dieter Jahn, Edingen-Neckarhausen; Michael Keil, Freinsheim; Walter Himmele, Walldorf; Bruno Wuerzer, Otterstadt, all of Fed. Rep. of Germany

[73] Assignee: BASF Aktiengesellschaft, Fed. Rep. of Germany

[21] Appl. No.: 628,319

[22] Filed: Jul. 6, 1984

[30] Foreign Application Priority Data

Jul. 8, 1983 [DE] Fed. Rep. of Germany ....... 3324707

[51] Int. Cl.⁴ ................. C07D 335/02; C07D 409/00; C07D 315/00; A01N 43/00
[52] U.S. Cl. .......................... 71/88; 549/28; 549/419; 549/426
[58] Field of Search ............ 549/419, 426, 28; 71/88

[56] References Cited

U.S. PATENT DOCUMENTS 3,950,420  4/1976  Sawaki et al. ................ 71/88
3,989,737  11/1976  Sawaki et al. ................ 71/90
4,422,864  12/1983  Becker et al. ................ 549/426

FOREIGN PATENT DOCUMENTS 3303182  8/1984  Fed. Rep. of Germany ........ 549/28

OTHER PUBLICATIONS

Chem. Abstracts 101:90967b (1984).
Chem. Abstracts 101:38468a (1984).

*Primary Examiner*—Ethel G. Love
*Attorney, Agent, or Firm*—Keil & Weinkauf

[57] ABSTRACT

Cyclohexane-1,3-dione derivatives of the formula

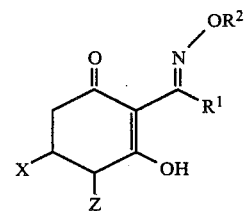

where $R^1$ is alkyl, $R^2$ is alkyl, unsubstituted or halogen-substituted alkenyl or alkynyl, X is a saturated or unsaturated five-membered or six-membered heterocyclic structure which carries one or more substituents, and Z is hydrogen, methoxycarbonyl, ethoxycarbonyl, methyl or cyano, and salts of these compounds are used for controlling undesirable plant growth.

10 Claims, No Drawings

CYCLOHEXANE-1,3-DIONE DERIVATIVES AND THEIR USE FOR CONTROLLING UNDESIRABLE PLANT GROWTH

The present invention relates to cyclohexane-1,3-dione derivatives, and herbicides which contain these compounds as active ingredients.

It has been disclosed that cyclohexane-1,3-dione derivatives can be used for controlling undesirable grasses (German Laid-Open Application DOS No. 3,121,355).

We have found that cyclohexane-1,3-dione derivatives of the formula

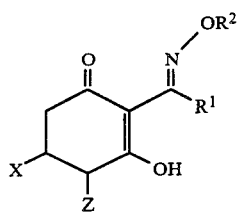

where $R^1$ is $C_1$–$C_4$-alkyl, $R^2$ is $C_1$–$C_4$-alkyl, unsubstituted or halogen-substituted $C_3$–$C_5$-alkenyl or $C_3$–$C_5$-alkynyl, X is a saturated or unsaturated five-membered or six-membered heterocyclic structure which is substituted by one or more $C_1$–$C_4$-alkoxy, $C_1$–$C_4$-alkylthio, $C_5$–$C_7$-cycloalkoxy or benzyloxy radicals or by an unsubstituted or substituted phenyl, phenoxy or phenylthio radical and may furthermore be substituted by alkyl, and Z is hydrogen, methoxycarbonyl, ethoxycarbonyl, methyl or cyano, and salts of these compounds, have an excellent action on plants from the grasses family and are highly selective in broad-leaved crops and in those crops which, although monocotyledonous, do not belong to the grasses. Moreover, compounds of the formula I include those which have a good action on grasses but at the same time possess selectivity in graminaceous crop plants, eg. cereal species.

The compounds of the formula I can occur in tautomeric forms, all of which are embraced by the patent claim:

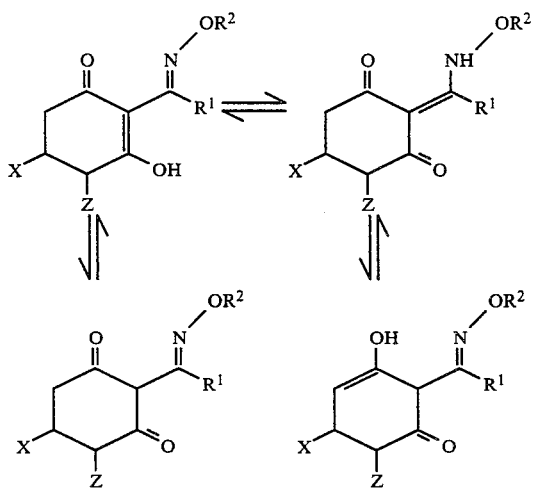

In the general formula I of the cyclohexane-1,3-dione derivatives, $R^1$ is branched or straight-chain alkyl of 1 to 4 carbon atoms, eg. methyl, ethyl, n-propyl, isopropyl, n-butyl, sec.-butyl, isobutyl or tert.-butyl, $R^2$ is branched or straight-chain alkyl of 1 to 4 carbon atoms, unsubstituted or halogen-substituted alkenyl of 3, 4 or 5 carbon atoms or alkynyl of 3, 4 or 5 carbon atoms, eg. methyl, ethyl, n-propyl, isopropyl, n-butyl, sec.-butyl, isobutyl, tert.-butyl, allyl, 3-chloroprop-2-enyl, 2-chloroprop-2-enyl, 1,2-dichloroprop-2-enyl, 1,1,2-trichloroprop-2-enyl or propargyl, X is a saturated or unsaturated five-membered or six-membered hetrocyclic structure which contains not more than two heteroatoms from the group consisting of O, N and S and preferably possesses not more than one double bond, such as tetrahydropyran, tetrahydrothiopyran, tetrahydrofuran or 1,4-dioxane radicals, eg. tetrahydropyran-2-yl, tetrahydropyran-3-yl, tetrahydrothiopyran-2-yl, tetrahydrothiopyran-3-yl, tetrahydrofuran-2-yl, tetrahydrofuran-3-yl or 1,4-dioxan-3-yl, each of which is substituted by $C_1$–$C_4$-alkoxy, such as methoxy, ethoxy, isopropoxy, n-propoxy, n-butoxy, isobutoxy, sec.-butoxy or tert.-butoxy, by $C_1$–$C_4$-alkylthio, such as methylthio, ethylthio, isopropylthio, n-propylthio, n-butylthio, sec.-butylthio, isobutylthio or tert.-butylthio, by $C_5$–$C_7$-cycloalkoxy, such as cyclopentyloxy or cyclohexyloxy, by benzyloxy, or by phenyl, phenoxy or phenylthio which is unsubstituted or substituted by halogen, $C_1$–$C_4$-alkyl or $C_1$–$C_4$-alkoxy, eg. phenyl, 4-chlorophenyl, 4-methylphenyl, 4-fluorophenyl, 4-methoxyphenyl, phenoxy, 4-chlorophenoxy, 4-fluorophenoxy, 4-methoxyphenoxy, 4-methylphenoxy, phenylthio, 4-chlorophenylthio, 4-fluorophenylthio, 4-methylphenylthio or 4-methoxyphenylthio, and may furthermore be substituted by not more than three alkyl radicals, such as methyl, ethyl, n-propyl, isopropyl, n-butyl, isobutyl, sec.-butyl or tert.-butyl, and Z is hydrogen, methoxycarbonyl, ethoxycarbonyl, methyl or cyano.

Preferred compounds of the formula I are those in which X is a saturated or unsaturated five-membered or six-membered heterocyclic structure which is substituted by one or more $C_1$–$C_4$-alkoxy radicals. Particularly preferred compounds of the formula I are those in which X is tetrahydropyranyl, and those in which Z is hydrogen.

Examples of suitable salts of the cyclohexane-1,3-dione derivatives of the formula I are alkali metal salts, such as potassium or sodium salts, alkaline earth metal salts, such as calcium, barium or magnesium salts, manganese, copper, zinc and iron salts and ammonium, phosphonium, sulfonium and sulfoxonium salts, eg. tetraalkylammonium, trialkylphosphonium, trialkylsulfonium or trialkylsulfoxonium salts, such as tetramethylammonium, tetraethylammonium, trimethylphosphonium, trimethylsulfonium or trimethylsulfoxonium salts.

The cyclohexane-1,3-dione derivatives of the formula I can be obtained by reacting a compound of the formula

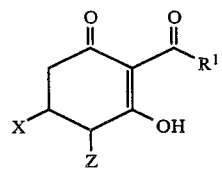

where $R^1$, X and Z have the above meanings, with a hydroxylamine derivative of the formula $R^2O$—$NH_3Y$, where $R^2$ has the above meanings and Y is any desired anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction proceeds particularly well at a pH of from 2 to 9, in particular from 4.5 to 5.5. The pH is advantageously established by adding acetates, for example alkali metal acetates, in particular sodium acetate or potassium acetate, or a mixture of the two salts. Alkali metal acetates are added in amounts of, for example, from 0.5 to 2 moles per mole of the ammonium compound of the formula $R^2O-NH_3Y$.

Examples of suitable solvents are dimethyl sulfoxide, alcohols, such as methanol, ethanol or isopropanol, benzene, hydrocarbons or chlorohydrocarbons, such as chloroform, dichloroethane, hexane or cyclohexane, esters, such as ethyl acetate, and ethers, such as dioxane or tetrahydrofuran. Mixtures of these solvents can also be used.

The reaction is complete after a few hours, and the product can then be isolated by evaporating down the mixture, adding water, extracting with a non-polar solvent, such as methylene chloride, and distilling off the solvent under reduced pressure.

The compounds of the formula I can also be obtained by reacting a compound of the formula II with a hydroxylamine of the formula $R^2O-NH_2$, where $R^2$ has the above meanings, in an inert diluent at from 0° C. to the boiling point of the reaction mixture, usually at from 0° to 80° C., preferably from 15° to 70° C. If necessary, the hydroxylamine can be used in the form of an aqueous solution.

Examples of suitable solvents for this reaction are alcohols, such as methanol, ethanol, isopropanol or cyclohexanol, hydrocarbons or chlorohydrocarbons, such as hexane, cyclohexane, methylene chloride, toluene or dichloroethane, esters, such as ethyl acetate, nitriles, such as acetonitrile, and cyclic ethers, such as tetrahydrofuran. Mixtures of these solvents can also be used.

The alkali metal salts of the cyclohexane-1,3-dione derivatives of the formula I can be obtained by treating these compounds with sodium hydroxide or potassium hydroxide in aqueous solution or in an organic solvent, such as methanol, ethanol or acetone. Sodium alcoholates and potassium alcoholates, too, can be used as bases.

The other metal salts, for example the manganese, copper, zinc, iron, calcium, magnesium and barium salts, can be prepared by reacting the sodium salts with the corresponding metal chlorides in aqueous solution. Ammonium, phosphonium, sulfonium or sulfoxonium salts can be prepared by reacting a compound of the formula I with ammonium, phosphonium, sulfonium or sulfoxonium hydroxide, if necessary in aqueous solution.

The compounds of the formula II can be prepared from cyclohexane-1,3-diones of the formula IV, which can also occur as the tautomeric forms of the formulae IVa and IVb

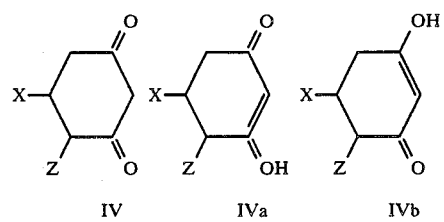

the preparation being carried out by a conventional method (Tetrahedron Lett. 29 (1975), 2491).

It is also possible to prepare compounds of the formula II via the enol-ester intermediates which are obtained, possibly as an isomer mixture, in the reaction of a compound of the formula IV, and undergo rearrangement in the presence of an imidazole or pyridine derivative (Japanese Preliminary Published Application No. 79/063052).

The compounds of the formula IV are obtained by conventional methods, as shown in the equations below:

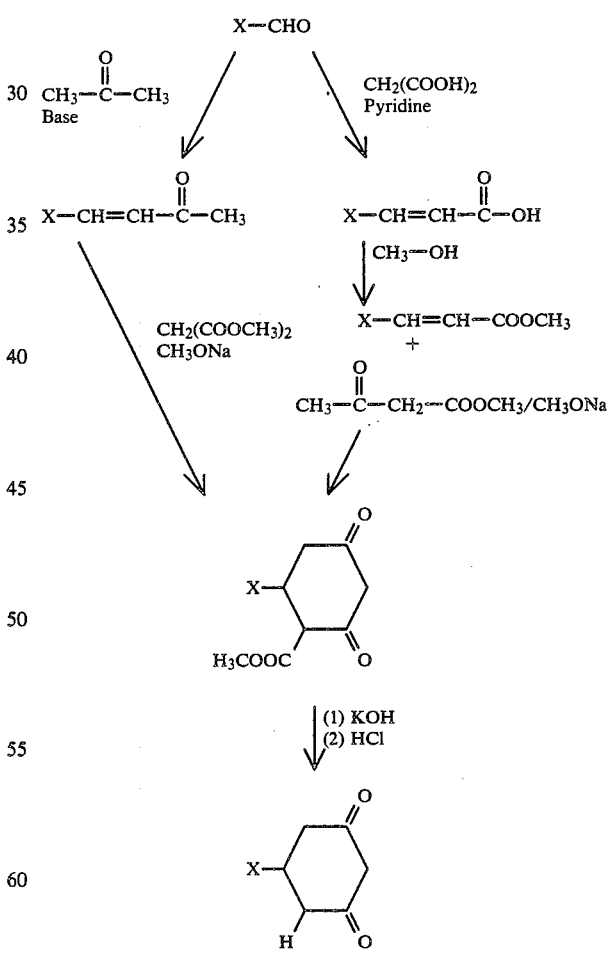

The Example which follows illustrates the preparation of the novel cyclohexane-1,3-dione derivatives of the formula I. Parts by weight bear the same relation to parts by volume as that of the kilogram to the liter.

EXAMPLE 1

10.2 parts by weight of 2-butyryl-5-(3-methyl-4-ethyl-6-isobutoxytetrahydropyran-2-yl)-cyclohexane-1,3-dione were dissolved in 100 parts by volume of ethanol, and 2.42 parts by weight of sodium acetate and 3.86 parts by weight of O-(3-chloroallyl)-hydroxylamine hydrochloride were added. The mixture was stirred for several hours at room temperature and then poured into ice-water, and the resulting mixture was extracted with methylene chloride. The methylene chloride phase was evaporated off, leaving 11.1 parts by weight of 2-(3-chloroallyloxyaminobutylidene)-5-(3-methyl-4-ethyl-6-isobutoxytetrahydropyran-2-yl)-cyclohexane-1,3-dione as a yellow oil of refractive index $n_D^{22}$ 1.5129.

The substances below can be prepared in a similar manner:

| No. | R | $R^1$ | $R^2$ | Z | $n_D$/m.p. [°C.] |
|---|---|---|---|---|---|
| 1 | 3-$CH_3$, 4-$C_2H_5$, 6-$OCH_2CH(CH_3)_2$ | $C_3H_7$ | $CH_2CH=CHCl$ | H | $n_D^{22}$ = 1.5129 |
| 2 | 3-$CH_3$, 4-$C_2H_5$, 6-$OCH_2CH(CH_3)_2$ | $C_3H_7$ | $C_2H_5$ | H | $n_D^{22}$ = 1.5006 |
| 3 | 3-$CH_3$, 4-$C_2H_5$, 6-$OCH_2CH(CH_3)_2$ | $C_3H_7$ | $CH_2CH=CH_2$ | $COOCH_3$ | $n_D^{23}$ = 1.5015 |
| 4 | 6-$OCH_3$ | $C_2H_5$ | $C_2H_5$ | H | $n_D^{27}$ = 1.5158 |
| 5 | 4-$C_6H_5$, 6-$OCH_3$ | $C_2H_5$ | $C_2H_5$ | H | |
| 6 | 6-$OCH_3$ | $C_3H_7$ | $C_2H_5$ | H | m.p. 69–71 |
| 7 | 3-$CH_3$, 4-$C_2H_5$, 6-$OCH_2CH(CH_3)_2$ | $C_2H_5$ | $C_2H_5$ | H | |
| 8 | 4-$C_6H_5$, 6-$OCH_3$ | $C_3H_7$ | $C_2H_5$ | H | |
| 9 | 3-$CH_3$, 4-$C_2H_5$, 6-$OCH_2(CH_3)_2$ | $C_3H_7$ | $CH_2CH=CH_2$ | H | $n_D^{22}$ = 1.5052 |
| 10 | 6-$OCH_3$ | $C_3H_7$ | $C_2H_5$ | $COOCH_3$ | $n_D^{26}$ = 1.5050 |
| 11 | 3-$C_2H_5$, 4-$C_3H_7$, 6-$OCH_3$ | $C_2H_5$ | $C_2H_5$ | H | |
| 12 | 4-$C_6H_5$, 6-$OCH_3$ | $C_3H_7$ | $CH_2CH=CH_2$ | H | |
| 13 | 3-$CH_3$, 4-$C_2H_5$, 6-$OCH_2CH(CH_3)_2$ | $C_2H_5$ | $CH_2CH=CH_2$ | H | |
| 14 | 6-$OCH_3$ | $C_2H_5$ | $CH_2CH=CH_2$ | H | $n_D^{25}$ = 1.5227 |
| 15 | 4-$C_6H_5$, 6-$OCH_3$ | $C_2H_5$ | $CH_2CH=CH_2$ | H | |
| 16 | 3-$C_2H_5$, 4-$C_3H_7$, 6-$OCH_3$ | $C_2H_5$ | $CH_2CH=CH_2$ | H | |
| 17 | 6-$OCH_3$ | $C_3H_7$ | $CH_2CH=CH_2$ | H | $n_D^{26}$ = 1.5164 |
| 18 | 3-$C_2H_5$, 4-$C_3H_7$, 6-$OCH_3$ | $C_3H_7$ | $C_2H_5$ | H | $n_D^{23}$ = 1.5080 |
| 19 | 6-$OCH_3$ | $C_2H_5$ | $CH_2CH=CHCl$ | H | |
| 20 | 3-$C_2H_5$, 4-$C_3H_7$, 6-$OCH_3$ | $C_3H_7$ | $CH_2CH=CH_2$ | H | $n_D^{23}$ = 1.5133 |
| 21 | 3-$CH_3$, 6-$OCH_3$ | $C_3H_7$ | $C_2H_5$ | H | |
| 22 | 6-$OCH_3$ | $C_3H_7$ | $CH_2CH=CH_2$ | $COOCH_3$ | $n_D^{30}$ = 1.5007 |
| 23 | 3-$CH_3$, 6-$OCH_3$ | $C_2H_5$ | $CH_2CH=CH_2$ | H | |
| 24 | 6-$OCH(CH_3)_2$ | $C_2H_5$ | $C_2H_5$ | H | |
| 25 | 6-$OCH(CH_3)_2$ | $C_2H_5$ | $CH_2CH=CH_2$ | H | |
| 26 | 3-$CH_3$, 6-$OCH_3$ | $C_3H_7$ | $CH_2CH=CH_2$ | H | |
| 27 | 3-$CH_3$, 6-$OCH_3$ | $C_3H_7$ | $C_2H_5$ | H | |
| 28 | 3-$CH_3$, 4-$C_2H_5$, 6-$OCH_3$ | $C_3H_7$ | $C_2H_5$ | H | |
| 29 | 3-$CH_3$, 6-$OC_2H_5$ | $C_3H_7$ | $C_2H_5$ | H | |
| 30 | 6-$OC_2H_5$ | $C_2H_5$ | $C_2H_5$ | H | |
| 31 | 3-$CH_3$, 4-$C_2H_5$, 6-$OCH(CH_3)_2$ | $C_3H_7$ | $C_2H_5$ | H | |
| 32 | 3-$CH_3$, 4-$C_2H_5$, 6-$OCH_3$ | $C_2H_5$ | $C_2H_5$ | H | |
| 33 | 3-$CH_3$6-$OC_2H_5$ | $C_3H_7$ | $CH_2CH=CH_2$ | H | |
| 34 | 4-$C_6H_5$, 6-$OCH(CH_3)_2$ | $C_2H_5$ | $C_2H_5$ | H | |
| 35 | 3-$CH_3$, 4-$C_2H_5$, 6-$OCH_3$ | $C_2H_5$ | $CH_2CH=CH_2$ | H | |
| 36 | 4-$C_6H_5$, 6-$OCH(CH_3)_2$ | $C_3H_7$ | $C_2H_5$ | H | |
| 37 | 3-$CH_3$, 4-$C_2H_5$, 6-$OC_2H_5$ | $C_3H_7$ | $C_2H_5$ | H | |
| 38 | 6-$OC_2H_5$ | $C_3H_7$ | $C_2H_5$ | H | $n_D^{21}$ = 1.5090 |
| 39 | 3-$CH_3$, 6-$OC_2H_5$ | $C_2H_5$ | $CH_2CH=CH_2$ | H | |
| 40 | 3-$CH_3$, 4-$C_2H_5$, 6-$OCH_3$ | $C_3H_7$ | $CH_2CH=CH_2$ | H | |
| 41 | 4-$C_6H_5$, 6-$OCH(CH_3)_2$ | $C_3H_7$ | $CH_2CH=CH_2$ | H | |
| 42 | 4-$C_6H_5$, 6-$OCH(CH_3)_2$ | $C_2H_5$ | $CH_2CH=CH_2$ | H | |
| 43 | 6-$OC_2H_5$ | $C_3H_7$ | $CH_2CH=CH_2$ | H | $n_D^{21}$ = 1.5150 |
| 44 | 6-$OC_2H_5$ | $C_2H_5$ | $CH_2CH=CH_2$ | H | |
| 45 | 3-$CH_3$, 6-$OC_2H_5$ | $C_2H_5$ | $C_2H_5$ | H | |
| 46 | 6-$OCH(CH_3)_2$ | $C_3H_7$ | $C_2H_5$ | H | |
| 47 | 6-$OCH(CH_3)_2$ | $C_3H_7$ | $CH_2=CH_2$ | H | |
| 48 | 3-$C_2H_5$, 4-$C_3H_7$, 6-$OC_2H_5$ | $C_3H_7$ | $C_2H_5$ | H | |
| 49 | 3-$C_2H_5$, 4-$C_3H_7$, 6-$OCH(CH_3)_2$ | $C_3H_7$ | $C_2H_5$ | H | |
| 50 | 4-$C_6H_5$, 6-$OC_2H_5$ | $C_3H_7$ | $C_2H_5$ | H | |
| 51 | 3-$C_2H_5$, 4-$C_3H_7$, 6-$OCH_2CH(CH_3)_2$ | $C_3H_7$ | $C_2H_5$ | H | |
| 52 | 3-$CH_3$, 6-$OCH(CH_3)_2$ | $C_2H_5$ | $C_2H_5$ | H | |
| 53 | 3-$CH_3$, 6-$OCH(CH_3)_2$ | $C_3H_7$ | $C_2H_5$ | H | |
| 54 | 3-$CH_3$, 6-$OCH(CH_3)_2$ | $C_2H_5$ | $CH_2CH=CH_2$ | H | |
| 55 | 6-$OC_6H_5$ | $C_3H_7$ | $C_2H_5$ | H | |
| 56 | 3-$C_2H_5$, 4-$C_3H_7$, 6-$OCH_2CH(CH_3)_2$ | $C_3H_7$ | $CH_2CH=CH_2$ | H | |
| 57 | 3-$CH_3$, 6-$OCH(CH_3)_2$ | $C_3H_7$ | $CH_2CH=CH_2$ | H | |

-continued

| No. | R¹ | R² | | Z | |
|---|---|---|---|---|---|
| 58 | 6-OC$_6$H$_5$ | C$_3$H$_7$ | CH$_2$CH=CH$_2$ | H | |
| 59 | 6-OC$_6$H$_5$ | C$_2$H$_5$ | C$_2$H$_5$ | H | |
| 60 | 6-OC$_6$H$_5$ | C$_2$H$_5$ | CH$_2$CH=CH$_2$ | H | |
| 61 | 3-C$_2$H$_5$, 4-C$_3$H$_7$, 6-OCH$_2$CH(CH$_3$)$_2$ | C$_2$H$_5$ | C$_2$H$_5$ | H | |
| 62 | 3-C$_2$H$_5$, 4-C$_3$H$_7$, 6-OCH$_2$CH(CH$_3$)$_2$ | C$_2$H$_5$ | CH$_2$CH=CH$_2$ | H | |
| 63 | 4-C$_6$H$_5$, 6-OC$_2$H$_5$ | C$_2$H$_5$ | C$_2$H$_5$ | H | |
| 64 | 6-OCH$_2$CH(CH$_3$)$_2$ | C$_2$H$_5$ | C$_2$H$_5$ | H | |
| 65 | 3-CH$_3$, 6-OCH$_2$CH(CH$_3$)$_2$ | C$_2$H$_5$ | C$_2$H$_5$ | H | |
| 66 | 6-OCH$_2$CH(CH$_3$)$_2$ | C$_3$H$_7$ | C$_2$H$_5$ | H | |
| 67 | 3-CH$_3$, 6-OCH$_2$CH(CH$_3$$_2$) | C$_3$H$_7$ | C$_2$H$_5$ | H | |
| 68 | 6-OCH$_2$C$_6$H$_5$ | C$_3$H$_7$ | C$_2$H$_5$ | H | |
| 69 | 6-OCH$_2$C$_6$H$_5$ | C$_3$H$_7$ | CH$_2$CH=CH$_2$ | H | |
| 70 | 4-C$_6$H$_5$, 6-OCH$_2$CH(CH$_3$)$_2$ | C$_2$H$_5$ | C$_2$H$_5$ | H | |
| 71 | 4-C$_6$H$_5$, 6-OC$_6$H$_4$Cl | C$_3$H$_7$ | C$_2$H$_5$ | H | |
| 72 | 4-C$_6$H$_5$, 6-OC$_6$H$_4$Cl | C$_3$H$_7$ | CH$_2$CH=CH$_2$ | H | |
| 73 | 6-SCH$_3$ | C$_2$H$_5$ | C$_2$H$_5$ | H | |
| 74 | 6-SC$_2$H$_5$ | C$_2$H$_5$ | C$_2$H$_5$ | H | |
| 75 | 6-SCH$_3$ | C$_2$H$_5$ | CH$_2$CH=CH$_2$ | H | |
| 76 | 6-SCH$_3$ | C$_3$H$_7$ | CH$_2$CH=CH$_2$ | H | |
| 77 | 6-SCH$_3$ | C$_3$H$_7$ | C$_2$H$_5$ | H | |
| 78 | 6-SC$_2$H$_5$ | C$_3$H$_7$ | C$_2$H$_5$ | H | |
| 79 | 6-SC$_2$H$_5$ | C$_3$H$_7$ | CH$_2$CH=CH$_2$ | H | |
| 80 | 6-SC$_2$H$_5$ | C$_2$H$_5$ | CH$_2$CH=CH$_2$ | H | |

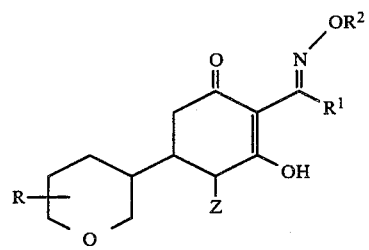

| 81 | 6-OCH$_3$ | C$_2$H$_5$ | C$_2$H$_5$ | H | |
|---|---|---|---|---|---|
| 82 | 6-SCH$_3$ | C$_2$H$_5$ | CH$_2$CH=CH$_2$ | H | |
| 83 | 6-SCH$_3$ | C$_2$H$_5$ | C$_2$H$_5$ | H | |
| 84 | 2-CH$_3$, 6-OCH$_3$ | C$_2$H$_5$ | C$_2$H$_5$ | H | |
| 85 | 2-CH$_3$, 6-OC$_2$H$_5$ | C$_2$H$_5$ | C$_2$H$_5$ | H | |
| 86 | 6-SCH$_3$ | C$_3$H$_7$ | C$_2$H$_5$ | H | |
| 87 | 2-CH$_3$, 6-OCH$_3$ | C$_2$H$_5$ | CH$_2$CH=CH$_2$ | H | |
| 88 | 2-CH$_3$, 6-OC$_2$H$_5$ | C$_2$H$_5$ | CH$_2$CH=CH$_2$ | H | |
| 89 | 6-SCH$_3$ | C$_3$H$_7$ | CH$_2$CH=CH$_2$ | H | |
| 90 | 6-OCH$_3$ | C$_3$H$_7$ | C$_2$H$_5$ | H | $n_D^{26} = 1.5163$ |
| 91 | 2-CH$_3$, 6-OCH$_3$ | C$_3$H$_7$ | CH$_2$CH=CH$_2$ | H | |
| 92 | 2-CH$_3$, 6-OCH$_3$ | C$_3$H$_7$ | C$_2$H$_5$ | H | |
| 93 | 2-CH$_3$, 6-OC$_2$H$_5$ | C$_3$H$_7$ | CH$_2$CH=CH$_2$ | H | |
| 94 | 6-OCH$_3$ | C$_3$H$_7$ | CH$_2$CH=CH$_2$ | H | $n_D^{25} = 1.5219$ |
| 95 | 6-OCH$_3$ | C$_2$H$_5$ | CH$_2$CH=CH$_2$ | H | |
| 96 | 2-CH$_3$, 6-OC$_2$H$_5$ | C$_3$H$_7$ | C$_2$H$_5$ | H | |
| 97 | 2-CH$_3$, 6-OCH$_2$CH(CH$_3$)$_2$ | C$_2$H$_5$ | C$_2$H$_5$ | H | |
| 98 | 2-CH$_3$, 6-OCH$_2$CH(CH$_3$)$_2$ | C$_3$H$_7$ | C$_2$H$_5$ | H | |
| 99 | 2-CH$_3$, 6-OCH(CH$_3$)$_2$ | C$_2$H$_5$ | C$_2$H$_5$ | H | |
| 100 | 2-CH$_3$, 6-OCH$_2$CH(CH$_3$)$_2$ | C$_2$H$_5$ | CH$_2$CH=CH$_2$ | H | |
| 101 | 2-CH$_3$, 6-OCH(CH$_3$)$_2$ | C$_2$H$_5$ | CH$_2$CH=CH$_2$ | H | |
| 102 | 2-CH$_3$, 6-OCH$_2$CH(CH$_3$)$_2$ | C$_3$H$_7$ | CH$_2$CH=CH$_2$ | H | |
| 103 | 2-CH$_3$, 6-OC$_6$H$_5$ | C$_2$H$_5$ | C$_2$H$_5$ | H | |
| 104 | 6-OC$_2$H$_5$ | C$_2$H$_5$ | C$_2$H$_5$ | H | |
| 105 | 2-CH$_3$, 6-OC$_6$H$_5$ | C$_2$H$_5$ | CH$_2$CH=CH$_2$ | H | |
| 106 | 6-OC$_2$H$_5$ | C$_2$H$_5$ | CH$_2$CH=CH$_2$ | H | |
| 107 | 6-OC$_2$H$_5$ | C$_3$H$_7$ | CH$_2$CH=CHCl | H | |
| 108 | 2-CH$_3$, 6-OC$_6$H$_5$ | C$_3$H$_7$ | C$_2$H$_5$ | H | |
| 109 | 2-CH$_3$, 6-OC$_6$H$_5$ | C$_3$H$_7$ | CH$_2$CH=CH$_2$ | H | |
| 110 | 6-SC$_2$H$_5$ | C$_3$H$_7$ | C$_2$H$_5$ | H | |
| 111 | 6-SC$_2$H$_5$ | C$_3$H$_7$ | CH$_2$CH=CH$_2$ | H | |
| 112 | 6-OC$_2$H$_5$ | C$_3$H$_7$ | C$_2$H$_5$ | H | |
| 113 | 6-OCH$_3$ | C$_3$H$_7$ | CH$_2$C≡CH | H | $n_D^{31} = 1.5269$ |
| 114 | 6-OC$_2$H$_5$ | C$_3$H$_7$ | CH$_2$CH=CH$_2$ | H | |
| 115 | 6-SC$_2$H$_5$ | C$_2$H$_5$ | C$_2$H$_5$ | H | |
| 116 | 6-OCH$_3$ | C$_3$H$_7$ | CH$_2$CH=CHCl | H | $n_D^{31} = 1.5317$ |
| 117 | 6-OCH$_3$ | C$_3$H$_7$ | C$_3$H$_7$ | H | $n_D^{31} = 1.5125$ |
| 118 | 6-SC$_2$H$_5$ | C$_2$H$_5$ | CH$_2$CH=CH$_2$ | H | |
| 119 | 2-CH$_3$, 4-C$_6$H$_5$, 6-OCH$_3$ | C$_3$H$_7$ | CH$_2$CH=CH$_2$ | H | |
| 120 | 2-CH$_3$, 4-C$_6$H$_5$, 6-OC$_2$H$_5$ | C$_3$H$_7$ | C$_2$H$_5$ | H | |
| 121 | 2-CH$_3$, 4-C$_6$H$_5$, 6-OCH$_3$ | C$_3$H$_7$ | C$_2$H$_5$ | H | |
| 122 | 2-CH$_3$, 4-C$_6$H$_5$, 6-OCH$_2$CH($_3$)$_2$ | C$_3$H$_7$ | CH$_2$CH=CH$_2$ | H | |
| 123 | 2-CH$_3$, 4-C$_6$H$_5$, 6-OCH$_2$(CH$_3$)$_2$ | C$_3$H$_7$ | C$_2$H$_5$ | H | |
| 124 | 2-CH$_3$, 4-C$_6$H$_5$, 6-OC$_2$H$_5$ | C$_3$H$_7$ | CH$_2$CH=CH$_2$ | H | |

-continued

| No. | R¹ | | R² | Z | |
|---|---|---|---|---|---|
| 125 | 2-OCH₃ | C₃H₇ | C₂H₅ | H | $n_D^{28} = 1.5135$ |
| 126 | 2-OC₂H₅ | C₃H₇ | CH₂CH=CH₂ | H | |
| 127 | 2-OCH₃ | C₃H₇ | CH₂CH=CH₂ | H | |
| 128 | 2-OCH₃ | C₂H₅ | C₂H₅ | H | |
| 129 | 2-OC₂H₅ | C₂H₅ | C₂H₅ | H | |
| 130 | 2-OC₂H₅ | C₂H₅ | CH₂CH=CH₂ | H | |
| 131 | 2-SCH₃ | C₃H₇ | C₂H₅ | H | |
| 132 | 2-OCH₃ | C₂H₅ | CH₂CH=CH₂ | H | |
| 133 | 2-SCH₃ | C₃H₇ | CH₂CH=CH₂ | H | |
| 134 | 2-SC₂H₅ | C₂H₅ | C₂H₅ | H | |
| 135 | 2-OC₂H₅ | C₃H₇ | C₂H₅ | H | |
| | | | | | $n_D$/Fp [°C.] |
| 136 | 2-SCH₃ | C₂H₅ | CH₂CH=CH₂ | H | |
| 137 | 2-SC₂H₅ | C₃H₇ | C₂H₅ | H | |
| 138 | 2-SC₂H₅ | C₂H₅ | CH₂CH=CH₂ | H | |
| 139 | 2-SC₂H₅ | C₃H₇ | CH₂CH=CH₂ | H | |
| 140 | 2-SCH₃ | C₂H₅ | C₂H₅ | H | |
| 141 | 2-OCH(CH₃)₂ | C₃H₇ | C₂H₅ | H | |
| 142 | 2-OCH₂CH(CH₃)₂ | C₃H₇ | C₂H₅ | H | |
| 143 | 2-OC₆H₅ | C₂H₅ | C₂H₅ | H | |
| 144 | 2-OC₆H₅ | C₃H₇ | C₂H₅ | H | |
| 145 | 2-OC₆H₅ | C₂H₅ | CH₂CH=CH₂ | H | |
| 146 | 2-OC₆H₅ | C₃H₇ | CH₂CH=CH₂ | H | |
| 147 | 6-OCH(CH₃)₂ | C₂H₅ | C₂H₅ | H | |
| 148 | 6-OCH₂CH(CH₃)₂ | C₂H₅ | C₂H₅ | H | |
| 149 | 6-OC₆H₅ | C₂H₅ | C₂H₅ | H | |
| 150 | 6-OC₂H₅ | C₂H₅ | CH₂CH=CH₂ | H | |
| 151 | 6-OC₆H₅ | C₃H₇ | C₂H₅ | H | |
| 152 | 6-OC₆H₅ | C₃H₇ | CH₂CH=CH₂ | H | |
| 153 | 4-SC₂H₅ | C₃H₇ | C₂H₅ | H | $n_D^{19} = 1.5428$ |
| 154 | 4-OCH₃ | C₂H₅ | C₂H₅ | H | |
| 155 | 4-SC₂H₅ | C₃H₇ | CH₂CH=CH₂ | H | $n_D^{19} = 1.5481$ |
| 156 | 4-OCH₃ | C₃H₇ | C₂H₅ | H | |
| | | | | | $n_D$/m.p. [°C.] |
| 157 | 4-OC₂H₅ | C₂H₅ | C₂H₅ | H | |
| 158 | 4-SCH₃ | C₂H₅ | C₂H₅ | H | |
| 159 | 4-OCH₃ | C₃H₇ | CH₂CH=CH₂ | H | |
| 160 | 4-OCH₃ | C₂H₅ | CH₂CH=CH₂ | H | |
| 161 | 4-SC₂H₅ | C₂H₅ | C₂H₅ | H | |
| 162 | 4-SC₂H₅ | C₂H₅ | CH₂CH=CH₂ | H | |
| 163 | 4-OC₂H₅ | C₂H₅ | CH₂CH=CH₂ | H | |
| 164 | 4-OC₂H₅ | C₃H₇ | C₂H₅ | H | |
| 165 | 4-SCH₃ | C₂H₅ | CH₂CH=CH₂ | H | |
| 166 | 4-OCH(CH₃)₂ | C₃H₇ | CH₂CH=CH₂ | H | |
| 167 | 4-OCH₂H₅ | C₃H₇ | CH₂CH=CH₂ | H | |
| 168 | 4-OCH₂CH(CH₃)₂ | C₃H₇ | C₂H₅ | H | |
| 169 | 4-SCH₃ | C₃H₇ | CH₂CH=CH₂ | H | |
| 170 | 2-CH₃, 4-C₆H₅, 6-OCH(CH₃)₂ | C₃H₇ | C₂H₅ | H | |
| 171 | 2-CH₃, 4-C₆H₅, 6-OCH(CH₃)₂ | C₂H₅ | C₂H₅ | H | |
| 172 | 2-CH₃, 4-C₆H₅, 6-OCH(CH₃)₂ | C₃H₇ | CH₂CH=CH₂ | H | |
| 173 | 4-SCH₃ | C₃H₇ | C₂H₅ | H | |
| 174 | 4-SC₆H₅ | C₃H₇ | C₂H₅ | H | |
| 175 | 4-OC₆H₅ | C₂H₅ | C₂H₅ | H | |

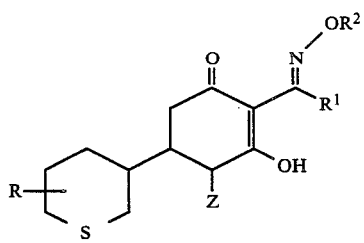

| 176 | 2-OCH₃ | C₂H₅ | C₂H₅ | H |
| 177 | 2-SCH₃ | C₂H₅ | CH₂CH=CH₂ | H |
| 178 | 2-SCH₃ | C₃H₇ | CH₂CH=CH₂ | H |
| 179 | 2-OCH₃ | C₂H₅ | CH₂CH=CH₂ | H |
| 180 | 2-OCH₃ | C₃H₇ | C₂H₅ | H |
| 181 | 2-OC₂H₅ | C₂H₅ | C₂H₅ | H |
| 182 | 2-OCH₃ | C₃H₇ | CH₂CH=CH₂ | H |
| 183 | 2-OC₂H₅ | C₂H₅ | CH₂CH=CH₂ | H |
| 184 | 2-SC₂H₅ | C₂H₅ | C₂H₅ | H |
| 185 | 2-SCH₃ | C₂H₅ | C₂H₅ | H |
| 186 | 2-SCH₃ | C₃H₇ | C₂H₅ | H |
| 187 | 4-SCH₃ | C₂H₅ | C₂H₅ | H |
| 188 | 2-SC₂H₅ | C₃H₇ | CH₂CH=CH₂ | H |
| 189 | 4-SCH₃ | C₂H₅ | CH₂CH=CH₂ | H |

-continued

| No. | | R¹ | R² | Z | |
|---|---|---|---|---|---|
| 190 | 2-OCH(CH₃)₂ | C₂H₅ | C₂H₅ | H | |
| 191 | 2-OC₆H₅ | C₂H₅ | C₂H₅ | H | |
| 192 | 2-SC₆H₅ | C₂H₅ | C₂H₅ | H | |
| 193 | 4-SCH₃ | C₃H₇ | C₂H₅ | H | |
| 194 | 4-SCH₃ | C₃H₇ | CH₂CH=CH₂ | H | |
| 195 | 4-OC₂H₅ | C₂H₅ | C₂H₅ | H | |
| 196 | 4-OC₂H₅ | C₂H₅ | CH₂CH=CH₂ | H | |
| 197 | 4-OCH₃ | C₃H₇ | CH₂CH=CH₂ | H | |
| 198 | 4-OCH₃ | C₃H₇ | C₂H₅ | H | |
| 199 | 4-SC₂H₅ | C₂H₅ | C₂H₅ | H | |
| 200 | 4-SC₄H₅ | C₂H₅ | CH₂CH=CH₂ | H | |
| 201 | 4-OCH₃ | C₂H₅ | C₂H₅ | H | |
| 202 | 4-SC₂H₅ | C₃H₇ | C₂H₅ | H | $n_D^{27} = 1.5637$ |
| 203 | 4-SC₂H₅ | C₃H₇ | CH₂CH=CH₂ | H | $n_D^{22} = 1.5672$ |
| 204 | 4-OCH₃ | C₂H₅ | CH₂CH=CH₂ | H | |
| 205 | 4-SC₆H₅ | C₃H₇ | C₂H₅ | H | |
| 206 | 4-OC₆H₅ | C₃H₇ | C₂H₅ | H | |

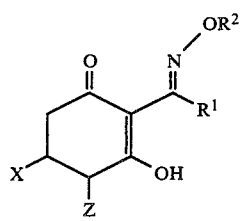

| No. | X | R¹ | R² | Z | |
|---|---|---|---|---|---|
| 207 | 2,5-dimethoxytetrahydrofuran-3-yl | C₂H₅ | C₂H₅ | H | |
| 208 | 2,5-dimethoxytetrahydrofuran-3-yl | C₂H₅ | CH₂CH=CH₂ | H | |
| 209 | 2,5-dimethoxytetrahydrofuran-3-yl | C₃H₇ | C₂H₅ | H | |
| 210 | 2,5-dimethoxytetrahydrofuran-3-yl | C₃H₇ | CH₂CH=CH₂ | H | |
| 211 | 2-methoxy-1,4-dioxan-3-yl | C₃H₇ | C₂H₅ | H | |
| 212 | 2-methoxy-1,4-dioxan-3-yl | C₃H₇ | CH₂CH=CH₂ | H | |
| 213 | 3-ethyl-6-isobutoxytetrahydropyran-2-yl | C₃H₇ | C₂H₅ | H | |
| 214 | 3-ethyl-6-isobutoxytetrahydropyran-2-yl | C₃H₇ | CH₂CH=CH₂ | H | |
| 215 | 6-cyclohexoxytetrahydropyran-2-yl | C₃H₇ | C₂H₅ | COOCH₃ | $n_D^{25} = 1.5093$ |
| 216 | 6-cyclohexoxytetrahydropyran-2-yl | C₃H₇ | CH₂CH=CH₂ | COOCH₃ | $n_D^{24} = 1.5138$ |
| 217 | 3-methyl-6-isobutoxytetrahydropyran-2-yl | C₃H₇ | C₂H₅ | COOCH₃ | $n_D^{25} = 1.5002$ |
| 218 | 3-methyl-6-isobutoxytetrahydropyran-2-yl | C₃H₇ | CH₂CH=CH₂ | COOCH₃ | $n_D^{26} = 1.4988$ |
| 219 | 3-methyl-6-isobutoxytetrahydropyran-2-yl | C₃H₅ | C₂H₅ | COOCH₃ | $n_D^{25} = 1.5007$ |
| 220 | 3-methyl-6-isobutoxytetrahydropyran-2-yl | C₂H₅ | CH₂CH=CH₂ | COOCH₃ | $n_D^{24} = 1.5060$ |
| 221 | 3-methyl-6-benzoxytetrahydropyran-2-yl | C₃H₇ | C₂H₅ | COOCH₃ | $n_D^{24} = 1.5294$ |
| 222 | 3-methyl-6-benzoxytetrahydropyran-2-yl | C₃H₇ | CH₂CH=CH₂ | COOCH₃ | $n_D^{24} = 1.5352$ |
| 223 | 6-benzoxytetrahydropyran-2-yl | C₃H₇ | C₂H₅ | COOCH₃ | $n_D^{26} = 1.5303$ |
| 224 | 6-benzoxytetrahydropyran-2-yl | C₃H₇ | CH₂CH=CH₂ | COOCH₃ | $n_D^{24} = 1.5382$ |
| 225 | 6-benzoxytetrahydropyran-2-yl | C₃H₇ | C₂H₅ | H | $n_D^{23} = 1.5418$ |
| 226 | 6-benzoxytetrahydropyran-2-yl | C₃H₇ | CH₂CH=CH₂ | H | $n_D^{23} = 1.5462$ |
| 227 | 3-methyl-6-isobutoxytetrahydropyran-2-yl | C₃H₇ | C₂H₅ | H | |
| 228 | 3-methyl-6-isobutoxytetrahydropyran-2-yl | C₃H₇ | CH₂CH=CH₂ | H | $n_D^{24} = 1.5047$ |
| 229 | 3-methyl-6-isobutoxytetrahydropyran-2-yl | C₂H₅ | C₂H₅ | H | $n_D^{24} = 1.5033$ |
| 230 | 3-methyl-6-isobutoxytetrahydropyran-2-yl | C₂H₅ | CH₂CH=CH₂ | H | $n_D^{24} = 1.5078$ |
| 231 | 6-cyclohexoxytetrahydropyran-2-yl | C₃H₇ | C₂H₅ | H | |
| 232 | 6-cyclohexoxytetrahydropyran-2-yl | C₃H₇ | CH₂CH=CH₂ | H | $n_D^{24} = 1.5218$ |

The cyclohexane-1,3-dione derivatives of the formula I, and salts thereof, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 9 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 17 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 6 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 116 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 117 is intimately mixed with 97 parts by weight of particulate kaolin. A dust is obtained containing 3% by weight of the active ingredient.

VII. 30 parts by weight of compound no. 169 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 153 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well when they are applied postemergence, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, the type of soil and the application method employed, and varied from 0.025 to 3 kg/ha and more, but is preferably from 0.1 to 1 kg/ha.

The herbicidal action of the cyclohexane-1,3-dione derivatives of the formula I is demonstrated in greenhouse experiments.

The vessels employed were plastic flowerpots having a volume of 300 cm³, and which were filled with a sandy loam containing about 1.5% humus. The seeds of the test plants were sown shallow, and separately, according to species. For the postemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were for example 0.25 and 0.5 kg of active ingredient per hectare.

The pots were set up in the greenhouse-species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides, Avena fatua, Bromus inermis, Echinochloa crus-galli, Glycine max., Hordeum vulgare, Lolium multiflorum, Setaria italica, Sorghum halepense,* and *Triticum aestivum.*

On preemergence application in the greenhouse, for example compounds nos. 2, 4, 9, 14, 17, 18, 90, 94, 113, 116, 117, 125 and 153, applied at a rate of 3 kg/ha, had a considerable herbicidal action on grasses.

On postemergence application, for instance compounds nos. 4, 6, 17, 38, 90, 94, 113, 116 and 117, applied at a rate of 0.25 kg/ha, were selectively herbicidally effective in broadleaved crops. Compounds nos. 2, 9 and 10 at 0.5 kg/ha, and nos. 153 and 155 at 0.25 kg/ha combatted for example unwanted grasses in cereals.

In view of the numerous application methods possible, the herbicides according to the invention, or agents containing them, may be used in a further large number of crops for removing unwanted wild grasses or grassy crop plants growing where they are not desired.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |

-continued

| Botanical name | Common name |
| --- | --- |
| Brassica napus var. napus | rapeseed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Phaseolus lunatus | limabeans |
| Phaseolus mungo | mungbeans |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | Sesame |
| Solanum tuberosum | Irish potatoes |
| Sorghum bicolor (s. vulgare) | sorghum |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the cyclohexane-1,3-dione derivatives of the formula I, or agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, other cyclohexane-1,3-dione derivatives, etc.

It may also be useful to apply the novel compounds, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. Cyclohexane-1,3-dione derivatives of the formula

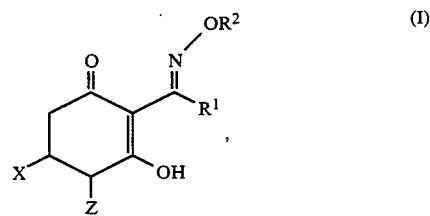

where $R^1$ is $C_1$-$C_4$-alkyl, $R^2$ is $C_1$-$C_4$-alkyl, unsubstituted or halogen-substituted $C_3$-$C_5$-alkenyl or $C_3$-$C_5$-alkynyl, X is a saturated or unsaturated six-membered heterocyclic structure having a ring which consists of carbon atoms and a hetero atom selected from the group consisting of O and S, possesses not more than one double bond and is substituted by one or more $C_1$-$C_4$-alkoxy, $C_1$-$C_4$-alkylthio, $C_5$-$C_7$-cycloalkoxy or benzyloxy radicals or by phenyl, phenoxy or phenylthio radical, each of which may be substituted by, halogen, $C_1$-$C_4$-alkyl, $C_1$-$C_4$-alkoxy and may furthermore be substituted by $C_1$-$C_4$-alkyl, and Z is hydrogen, methoxycarbonyl, methyl or cyano, and salts thereof.

2. Cyclohexane-1,3-dione derivatives of the formula I as defined in claim 1, where X is a saturated or unsaturated six-membered heterocyclic structure which is substituted by at least one $C_1$-$C_4$-alkoxy radical.

3. Cyclohexane-1,3-dione derivatives of the formula I as defined in claim 1, where Z is hydrogen and X is tetrahydrothiopyranyl substituted by a $C_1$-$C_4$-alkylthio group.

4. Cyclohexane-1,3-dione derivatives of the formula I as defined in claim 1, where X is substituted tetrahydropyranyl.

5. Cyclohexane-1,3-dione derivatives of the formula I as defined in claim 1, where $R^1$ is ethyl, $R^2$ is ethyl, X is 6-methoxytetrahydropyran-2-yl and Z is hydrogen.

6. A herbicide containing inert additives and a herbicidally effective amount of a cyclohexane-1,3-dione derivative of the formula I as defined in claim 1.

7. A herbicide as defined in claim 6, where the cyclohexane-1,3-dione derivative of the formula I is one where X is a saturated or unsaturated six-membered heterocyclic structure which is substituted by at least one $C_1$-$C_4$-alkoxy radical.

8. A herbicide as defined in claim 6, where the cyclohexane-1,3-dione derivative of the formula I is one where Z is hydrogen.

9. A herbicide as defined in claim 6, where the cyclohexane-1,3-dione derivative of the formula I is one where X is substituted tetrahydropyranyl.

10. A process for combating the growth of unwanted plants, wherein the unwanted plants or the area to be kept free from unwanted plant growth are treated with a herbicidally effective amount of a cyclohexane-1,3-dione derivative of the formula I as defined in claim 1.

* * * * *